United States Patent [19]

Hirschfeld et al.

[11] 4,169,137

[45] Sep. 25, 1979

[54] ANTIGEN DETECTING REAGENTS

[75] Inventors: Tomas Hirschfeld, Framingham, Mass.; Diane Eaton, Aylesbury, England

[73] Assignee: Block Engineering, Inc., Cambridge, Mass.

[21] Appl. No.: 535,111

[22] Filed: Dec. 20, 1974

[51] Int. Cl.² ............... A61K 29/00; G01N 31/00; G01N 31/22; G01N 33/16

[52] U.S. Cl. .......................... 424/8; 424/3; 424/7; 424/2; 424/12; 23/230 B; 260/6; 260/112 R

[58] Field of Search .............. 424/3, 7, 8, 12; 260/6, 260/112 R; 250/461 B, 459; 23/230 B

[56] References Cited

U.S. PATENT DOCUMENTS

| | | | |
|---|---|---|---|
| 3,553,310 | 1/1971 | Csizmas et al. | 424/8 |
| 3,639,558 | 2/1972 | Csizmas et al. | 424/12 |
| 3,641,235 | 2/1972 | Weiss | 424/8 |
| 3,789,116 | 1/1974 | Kay | 424/8 |
| 3,796,634 | 3/1974 | Haynes et al. | 195/63 |
| 3,853,987 | 12/1974 | Dreyer | 424/8 |
| 3,970,597 | 7/1976 | Sokolovsky | 260/6 |

OTHER PUBLICATIONS

Nature, vol. 249, No. 5452, pp. 81–83, May 3, 1974.
Ungar–Waron, CA. vol. 74, 1973, No. 103454m.

*Primary Examiner*—Donald B. Moyer
*Attorney, Agent, or Firm*—Schiller & Pandiscio

[57] ABSTRACT

Antigen-detecting reagents, suitable for detection of antigens present in liquids, biological fluids and tissues are prepared by covalently linking a large number of fluorescent dye molecules to the appropriate antibody through a polymeric backbone possessing reactive functional groups along the length of the chain.

15 Claims, No Drawings

ANTIGEN DETECTING REAGENTS

The present invention relates to a reagent useful for the detecting of antigens present in liquids, biological fluids and tissues, to the method of using that reagent for the stated purpose, and to methods for the manufacture of said reagent.

Methods currently available for the detection of antigenic materials in biological fluids and tissues suffer from a number of serious disadvantages. Primary among those handicaps is the lack of sensitivity sufficient to discern small numbers of the antigen molecules. Many cases of serious diseases having an antigenic etiology thus remain unnoticed, thereby resulting in unnecessary suffering and, ultimately, in death. Another disadvantage of present methods for antigen detection resides in the nature of the reagent used. Those prior art reagents contain radioisotopic materials, thus present a potential hazard to the laboratory people carrying out the assay.

The technique of detecting and classifying antigenic materials in biological fluids and tissues by exposure of that fluid or tissue to a specific antibody to which has been attached a radiant energy emitter is known in the art. This method depends upon the ability of the observer to distinguish between the antigen-tagged antibody complex and the uncomplexed tagged antibodies. For this purpose various radiant energy detection instruments may be utilized, depending upon the nature of the emitter itself. When the emission results from a fluorescent agent, e.g. a fluorescent dye such as fluorescein, rhodamine, pyronine, eosin, acridine, acrifalvine, seprinine, methylene blue, etc., appropriate optical fluorescent emission detection instruments, e.g. photometric devices, are suitably employed.

As is discussed hereinbefore, prior art methods for the detection of antigenic materials in animal body fluids suffer from a number of serious disadvantages, among which is the lack of sufficient sensitivity to detect very small quantities of the antigen. The present invention overcomes that problem by a novel, advantageous procedure which utilizes a reagent comprising an antibody molecule to which has been chemically attached a large number of fluorescent dye molecules through a polymer backbone having reactive functional groups along the length of its chain. By virtue of the presence of a multiplicity of fluorescent moieties, the antigen-antibody complex in very small quantities, i.e. as little as a single molecule, provided that the molecule is attached to a suitable substratum, e.g. a cell or cellular component, can be visualized by use of an appropriate photometric instrument. The present method is further advantageous over prior art procedures in that it avoids the use of radioactive reagents.

The reagent of the present invention generally comprises an antibody specific for the antigen to be detected, to which antibody has been covalently attached a primary-amine-containing polyfunctional polymeric backbone having coupled thereto a plurality of fluorescent dye molecules, the number of fluorescent dye molecules being limited so as not to prevent formation of the antibody-antigen complex to be visualized. The polyfunctional polymeric backbone and the antibody are bound to each other through a dialdehyde which is covalently bound to both the primary amine on the polyfunctional polymeric backbone, and to a primary amine moiety on the antibody.

Preferred embodiments are antigen-detecting reagents wherein the primary-amine-containing polyfunctional polymeric backbone is polyethyleneimine or polylysine, the fluorescent dye is fluorescein isothiocyanate or sulfonyl chloride of Lissamine Rhodamine-B, and the dialdehyde is glutaraldehyde.

Further preferred embodiments are antigen-detecting reagents wherein the primary-amine-containing polyfunctional polymeric backbone is polyethyleneimine, the fluorescent dye is fluorescein, and the dialdehyde is glutaraldehyde.

Most preferred embodiments are antigen-detecting reagents wherein the primary-amine-containing polyfunctional polymer backbone is polyethyleneimine having a molecular weight of about 20,000, the fluorescent dye is about 120 molecules of fluorescein isothiocyanate covalently bound to the polyethyleneimine, and the dialdehyde is glutaraldehyde.

It is essential in the practice of the present invention to limit the number of radiant energy emitting molecules to be attached to the antibody within a range which will not result in inhibition of formation of the antigen-antibody complex or interference with useful spectral properties. The polymer backbone has covalent bonding sites separated by a sufficient distance to avoid disruption of the useful spectral properties of the dye moieties caused by perturbation effects of one dye molecule interacting through space with another dye molecule.

Primary-amine-containing polymer backbone molecules suitable for the practice of this invention are polyethylenimines, suitably of molecular weight in the range of 1200–60,000, polylysines and other polymeric materials having a primary amine and containing repeating reactive functional groups along the length of their chain.

Dialdehydes of the formula

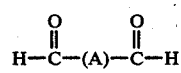

wherein A is an alkylene containing 0–7 carbon atoms are suitable dialdehydes. Glutaraldehyde is preferred.

Dialdehydes are particularly advantageous for binding a primary-amine-containing polyfunctional polymeric backbone to an antibody in that the reaction of the aldehyde provides differential functionality on the polymer whereby the fluorescent dye may be selectively reacted with other functional cites in the polymer chain and at a later time the unbound aldehyde moiety may be bound to an antibody. The dialdehyde therefore serves as both a blocking group and as a functionalizing group for further reaction.

In the practice of the present invention the primary-amine-containing polymeric backbone is allowed to react with the fluorescent dye which has been functionalized so as to enable it to react covalently with the repeating functional groups of the polymeric material. Prior to reaction with the functionalized fluorescent dye molecule, the primary amine of the polymeric substance is reacted with a dialdehyde in order to block the reactive amine end group of the polymer and at the same time provide functionality for further covalent bonding with the antibody. Glutaraldehyde is the preferred dialdehyde.

The following scheme sets out the method of forming a suitable antigen detecting reagent having a polyethylenimine backbone:

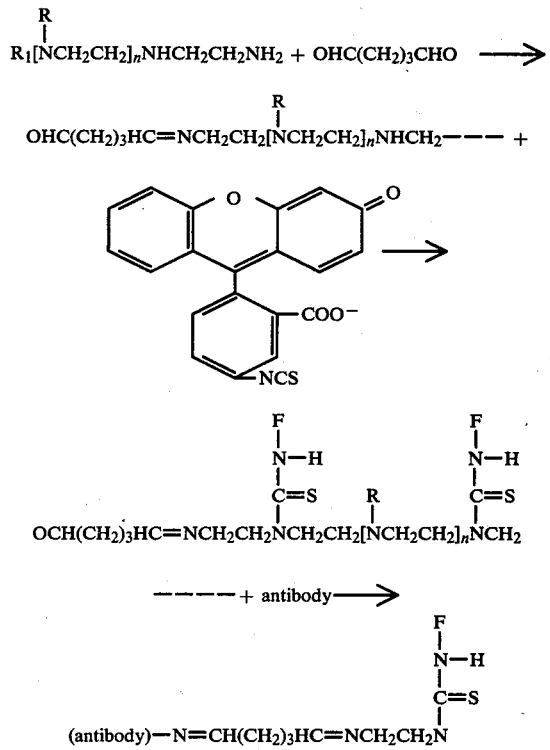

Wherein:
R = H or $[CH_2CH_2NH]_nCH_2CH_2NH_2$
$R_1 = H_2NCH_2CH_2-$
F = Fluorescein Preparation of the reagents of the present invention is exemplified by the reaction of polyethylenimine 200 (molecular weight 20,000) with glutaraldehyde in the presence of sodium cacodylate, reaction of the resulting imine with fluoroscein isothiocyanate and reaction of that dye tagged polymer with Anti-Echo 12 virus antiserum.

Typical antigens detected by the process of this invention are Hepatitis B antigen, Echo 12 virus antigen, Hoof and Mouth disease virus antigen, and Swine vesicular disease virus antigen. It will be recognized, however, that the present process is not limited to the detection of those antigens specifically named but is generally applicable to all antigens for which the appropriate antibody is available.

Thus, the present invention encompasses a method for the manufacture of the antigen-detecting diagnostic which comprises reacting the primary-amine-containing polyfunctional polymeric backbone with a dialdehyde, reacting functionalized fluorescent dye molecules with the protected polyfunctional polymeric backbone to form a dye tagged polymer and then reacting the dye tagged polymer with an appropriate antibody.

This method is exemplified by an antigen-detecting reagent wherein the functionalized fluorescent dye molecule is fluoroscein isothiocyanate, the dialdehyde is glutaraldehyde, the primary-amine-polyfunctional polymeric backbone is polyethylenimine of molecular weight 20,000 and the number of said fluorescent dye molecules is approximately 120.

Also encompassed is a method for the detection of antigens in biological fluids and tissues which method comprises mixing with a sample of biological fluid or tissue, a diagnostic reagent as earlier described; this method of the present invention is particularly applicable to determining Hepatitis B antigen in blood samples.

The invention will appear more fully from the examples which follow. These examples are given by way of illustration only and are not to be construed as limiting the invention either in spirit or in scope as many modifications both in materials and in methods will be apparent to those skilled in the art.

EXAMPLE 1

To a solution of 2 mg. of polyethylenimine 200 (molecular weight 20,000) in 1 ml. of 0.1 M sodium cacodylate at pH 7.0, 0.1 ml. of 25% aqueous glutaraldehyde is added with vigorous stirring. The resulting yellow reaction mixture is stirred for about 5 minutes and excess glutaraldehyde then removed by passage through a Sephadex G-25 (0.9×15 cm.) (silica gel) column. The column is eluted with 0.5 M, pH 9.5 aqueous sodium carbonate buffer and to the eluate is added 50 mg. of fluoroscein isothiocyanate dissolved in 1 m. of aqueous 0.5 M, pH 9.5 sodium carbonate buffer. The mixture is stirred continuously during the addition and stirring continued for about 16 hours, during which time the mixture is excluded from light. The excess dye is removed by passage through a Sephadex G-25 (silica gel) column (0.9×30.0 cm.) and subsequent elution of the column with 0.1 m, pH 7.0 aqueous sodium cacodylate. 2 Ml. fractions are collected.

The resulting polymer/dye complex is analyzed by the Folin-Ciocaulteau protein assay. That assay gives a linear curve with polyethylenimine, thus is suitable for estimation of the amount of polymer present. The Extinction Coefficient of fluoroscein isothiocyanate at 495 nm. is $73 \times 10^3$ and drops to 75% of this value on binding. By measuring both polymer and dye present in a given sample of the complex, the degree of dye binding is estimated. This degree of binding depends upon the dye concentration in the initial reaction mixture and different complexes are separated from different regions of the gel filtration column. The complex prepared by the process of this Example contains approximately 120 dye molecules per molecule of polyethylenimine.

EXAMPLE 2

When the procedure of Example 1 is repeated, substituting polyethylenimine 600 (molecular weight 60,000), the polymer/dye complex obtained contains approximately 130 dye molecules per molecule of polyethylenimine.

EXAMPLE 3

Polymer/dye complexes containing approximately 65 and 80 molecules, respectively, of dye per molecule of polyethylenimine 200 are produced also by appropriate modification of the procedure of Example 1.

EXAMPLE 4

Anti-Echo 12 virus antiserum (2.5 mg) is dissolved in 0.1 M, pH 7.0 aqueous sodium cacodylate and 0.65 mg. of the polymer/dye complex of Example 1 is added with stirring. The resultant mixture is stirred for 10 minutes at room temperature. Then tris (hydroxy methyl) amino methane (1 mg) is added to block any unreacted aldehyde groups and to prevent antibody crosslinking. The mixture is applied to a Sephadex G-200 column (0.9×60 cm) (dextran gel) equilibrated with 0.1 M, pH 8.2 tris/chloride buffer. The column is eluted with the same buffer and 2 ml. fractions are collected.

The optical density of the reagent and of the fractions is determined at 280 nm. and 495 nm. By difference spectral analysis the amount of antibody in each fraction is determined and the amount of antibody in each fraction is determined and the amount of dye bound per antibody molecule is estimated. Knowing the number of dye molecules per polymer molecule, the average number of polymer molecules per antibody molecule is calculated. By this assay procedure it was determined the 1.2–1.3 polymer molecules are bound to each antibody molecule.

The immunological activity of the dye/polymer/antibody complex is measured by hemagglutination. By this method it was found that the dye/polymer/antibody complex retained 70% of the activity of the uncombined antibody.

The fluorescence of the dye/polymer/antibody complex is obtained using an Aminco Bowan fluorimeter. Fluorescence is measured in relation to standard solutions of fluoroscein isothiocyanate of concentration 0.001–1.0 $\mu$gs/ml. Excitation is measured at 495 nm. and emission at 526 nm. Complexes are diluted to give the same optical density of 495 nm. as do the known dilutions of fluoroscein isothiocyanate. The quantum efficiency was determined as 4% for the complex containing polyethylenimine with 80 dye molecules and 2.4% for the complex containing polyethylenimine with 100 dye molecules, both of these values using free fluoroscein isothiocyanate as 100%.

EXAMPLE 5

Ths substitution of rhodamine isothiocyanate or rhodamine sulfonyl chloride in the procedure of Example 1 results in the corresponding rhodamine/polymer/antibody complexes.

EXAMPLE 6

To examine the reactivity of the dye/polymer/antibody of the invention, a solution is made of $3.44 \times 10^{-8}$ mole of Australian antigen (also known as Hepatitis B antigen) dissolved in 0.1 M tris amine hydrochloride buffer. A complex of dye/polymer/antibody is prepared in accordance with Example 3 and Example 4 using polyethylenimine 200 as the backbone, fluorescein isothiocyanate as the dye and a commercially available antibody to Australian antigen. The proportions are adjusted so that the complex contains about 70 molecules of dye per molecule of polyethylenimine. The fraction containing a 1:1 ratio of polyethylenimine molecules to antibody is separated in a Sephadex column. The resulting fraction exhibits a concentration of 340 mg/ml of protein, i.e. $2.2 \times 10^{-9}$ mols of tagged antibody. The fraction is mixed in molar ratios of 100:1, 10:1 and 1:1 antibody to antigen and each mixture exposed to radiation which will excite fluorescence in the due. The mixture at the 100:1 ratio exhibits about the same fluorescent characteristics as the tagged antibody per se, only very low intensity emissions being observed. The mixture at 10:1 ratio shows some larger sources of emission and the mixture at 1:1 exhibits even more higher brightness sources. Generally, with increasing proportion of antigen, the set of higher brightness sources increases in number, these latter sources being believed to indicate antigen coupled to a plurality of antibodies.

Since certain changes may be made in the above process and product without departing from the scope of the invention herein involved, it is intended that all matter contained in the above description shall be interpreted in an illustrative and not in a limiting sense.

What is claimed is:

1. An antigen-detecting reagent suitable for detection of antigens present in liquid, biological fluids and tissues, said reagent comprising an antibody specific for the antigen to be detected and having a primary amine moiety;

a primary-amine-containing polyfunctional polymeric backbone molecule which has been covalently attached to said antibody;

said backbone molecule having coupled thereto a plurality of fluorescent dye radicals, the number of said fluorescent dye radicals being limited so as not to prevent formation of a complex between said antibody with said backbone molecule and said antigen, said polyfunctional polymeric backbone molecule and said antibody being attached by a dialdehyde which is covalently bound both to the primary amine of said polyfunctional polymeric backbone molecule and to said primary amine moiety of said antibody.

2. The reagent of claim 1 wherein said polyfunctional polymeric backbone molecule is polyethylenimine or polylysine, said fluorescent dye is fluoroscein isothiocyanate or sulfonyl chloride of Lissamine Rhodamine-B, and said dialdehyde is glutaraldehyde.

3. The reagent of claim 1 wherein said polyfunctional polymeric backbone molecule is polyethylenimine, said fluorescent dye is fluorescein, and said dialdehyde is glutaraldehyde.

4. The reagent of claim 1 wherein said polyfunctional polymer backbone molecule is polyethylenimine having a molecular weight of about 20,000, said fluorescent dye radicals are fluorescein isothiocyanate covalently bound to each polyethylenimine molecule is a ratio of from about 65:1 to 120:1 and said dialdehyde is glutaraldehyde.

5. The reagent of claim 1 wherein said fluorescent dye radical are fluorescein.

6. The reagent of claim 1 wherein said polyfunctional polymeric backbone molecule is a polyethylenimine of molecular weight in the range of 1200–60,000.

7. The reagent of claim 1 wherein said polyfunctional polymeric backbone molecule is a polyethylenimine of molecular weight 1200.

8. The reagent of claim 1 wherein said polyfunctional polymeric backbone molecule is a polyethylenimine of molecular weight 20,000.

9. The reagent of claim 1 wherein said polyfunctional polymeric backbone molecule is a polylysine.

10. The reagent of claim 1 wherein said antibody is that which is specific to Hepatitis B antigen.

11. The reagent of claim 1 wherein said antibody is that which is specific to Anti-Echo virus.

12. The reagent of claim 1 wherein said antibody is that which is specific to Anti-Echo virus, said polyfunctional polymeric backbone molecule is a polyethylenimine of molecular weight 20,000, said fluorescent dye radicals are fluoroscein and the number of said fluorescent dye radicals bound to each said backbone molecule is approximately 120.

13. A method for the manufacture of an antigen-detecting diagnostic reagent, which comprises
reacting polyethylenimine of molecular weight of about 20,000 with glutaraldehyde sufficient to provide a protected polyfunctional polymeric backbone,
reacting sufficient functionalized molecules of fluoroscein isothiocyanate with said protected polyfunctional polymeric backbone to form a dye-tagged polymer having about 120 molecules of dye coupled to each said polymeric backbone; and
then reacting said dye-tagged polymer with an appropriate antibody.

14. A method for the detection of antigens in liquid which comprises mixing with a sample of said liquid a diagnostic reagent as described in claim 1.

15. The method for the detection of antigens in liquid which comprises mixing with a sample of said liquid a diagnostic reagent as described in claim 4.

* * * * *

UNITED STATES PATENT OFFICE
CERTIFICATE OF CORRECTION

Patent No. 4,169,137          Dated September 25, 1979

Inventor(s) Tomas Hirschfeld and Diane Eaton

It is certified that error appears in the above-identified patent and that said Letters Patent are hereby corrected as shown below:

Claim 4, column 6, line 42, "is" should be --in--.

*Signed and Sealed this*

*Eleventh* Day of *December 1979*

[SEAL]

*Attest:*

SIDNEY A. DIAMOND

*Attesting Officer*   *Commissioner of Patents and Trademarks*